(12) United States Patent
Montalbano et al.

(10) Patent No.: US 10,865,169 B2
(45) Date of Patent: Dec. 15, 2020

(54) LIQUID PHASE ISOMERIZATION PROCESS INTEGRATION

(71) Applicant: UOP LLC, Des Plaines, IL (US)

(72) Inventors: Joseph A. Montalbano, Elmhurst, IL (US); Patrick C. Whitchurch, Sleepy Hollow, IL (US); Gregory R. Werba, Arlington Heights, IL (US); Ian G. Horn, Streamwood, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/598,140

(22) Filed: May 17, 2017

(65) Prior Publication Data

US 2017/0349508 A1 Dec. 7, 2017

Related U.S. Application Data

(60) Provisional application No. 62/347,018, filed on Jun. 7, 2016.

(51) Int. Cl.
*C07C 7/12* (2006.01)
*C10G 59/02* (2006.01)
(Continued)

(52) U.S. Cl.
CPC ............... *C07C 7/12* (2013.01); *B01D 3/141* (2013.01); *C07C 5/2708* (2013.01);
(Continued)

(58) Field of Classification Search
CPC .................................................... C07C 7/12
See application file for complete search history.

(56) References Cited

U.S. PATENT DOCUMENTS 6,740,788 B1  5/2004  Maher et al.
2011/0263918 A1* 10/2011  Ou ........................ B01J 29/40
                                                              585/481
(Continued)

FOREIGN PATENT DOCUMENTS

WO    2008083021 A1    7/2008
WO    2013085681 A1    6/2013
(Continued)

OTHER PUBLICATIONS

Search Report dated Sep. 7, 2017 for corresponding PCT Appl. No. PCT/US2017/034413.

*Primary Examiner* — In Suk C Bullock
*Assistant Examiner* — Alyssa L Cepluch

(57) ABSTRACT

Processes and apparatuses for producing a $C_8$ aromatic isomer product are provided. The process comprises introducing a reformate stream comprising aromatic hydrocarbons to a reformate splitter column to provide a plurality of streams. One or more streams comprising at least one stream from the plurality of streams is passed to a reformate upgrading unit to obtain an upgraded reformate stream. The upgraded reformate stream is passed to an aromatics stripper column to provide an aromatics stripper sidedraw stream comprising $C_8$ aromatic hydrocarbons. The aromatics stripper sidedraw stream is passed to a xylene separation unit to provide the $C_8$ aromatic isomer product and a raffinate product stream. At least a portion of the raffinate product stream is processed in a liquid phase isomerization unit to obtain an isomerized stream.

11 Claims, 1 Drawing Sheet

(51) Int. Cl.
*C10G 61/06* (2006.01)
*C07C 5/27* (2006.01)
*B01D 3/14* (2006.01)

(52) U.S. Cl.
CPC ............ *C07C 5/2775* (2013.01); *C10G 59/02* (2013.01); *C10G 61/06* (2013.01); *Y02P 20/10* (2015.11)

(56) References Cited

U.S. PATENT DOCUMENTS

| | | | | |
|---|---|---|---|---|
| 2015/0094507 | A1* | 4/2015 | Gattupalli | C07C 7/005 585/470 |
| 2015/0376086 | A1* | 12/2015 | Tinger | B01J 19/2445 585/314 |
| 2015/0376088 | A1* | 12/2015 | Molinier | B01J 19/2445 585/314 |
| 2016/0046544 | A1* | 2/2016 | Molinier | C07C 5/2732 585/319 |

FOREIGN PATENT DOCUMENTS

| | | | |
|---|---|---|---|
| WO | 2015088631 | A1 | 6/2015 |
| WO | 2016003612 | A1 | 1/2016 |

* cited by examiner

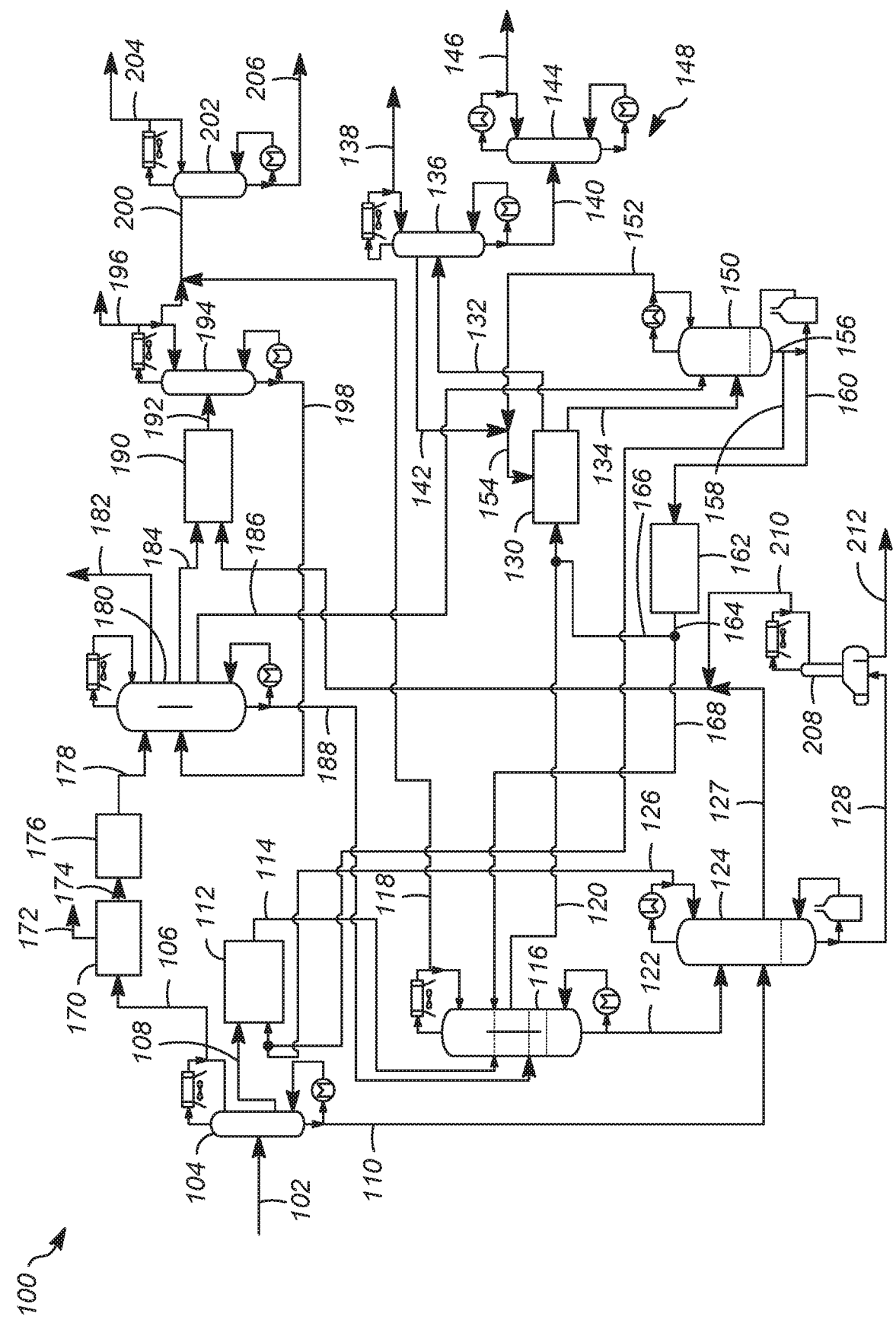

LIQUID PHASE ISOMERIZATION PROCESS INTEGRATION

CROSS-REFERENCE TO RELATED APPLICATION

This application claims priority from Provisional Application No. 62/347,018 filed Jun. 7, 2016, the contents of which cited application are hereby incorporated by reference in its entirety.

TECHNICAL FIELD

The technical field generally relates to apparatuses and processes for producing a $C_8$ aromatic isomer product in an aromatics complex. More particularly, the technical field relates to apparatuses and processes for producing para-xylene in an aromatic complex with integration of liquid phase isomerization and reformate upgrading process into the aromatics complex.

BACKGROUND

Most new aromatics complexes are designed to maximize the yield of benzene and $C_8$ aromatic isomer (para-xylene, meta-xylene, ethylbenzene and ortho-xylene). Benzene is a versatile petrochemical building block used in many different products based on its derivation including ethylbenzene, cumene, and cyclohexane. In many instances, the sought $C_8$ aromatic isomer is para-xylene as para-xylene is an important building block, which is used almost exclusively for the production of polyester fibers, resins, and films formed via terephthalic acid or dimethyl terephthalate intermediates. Accordingly, an aromatics complex may be configured in many different ways depending on the desired products, available feedstocks, and investment capital available. A wide range of options permits flexibility in varying the product slate balance of benzene and para-xylene to meet downstream processing requirements.

A prior art aromatics complex flow scheme has been disclosed by Meyers in the HANDBOOK OF PETROLEUM REFINING PROCESSES, 2d. Edition in 1997 by McGraw-Hill.

In an aromatics complex, the production of commercial-grade $C_8$ aromatic isomers involves multiple separation steps such as fractionation, adsorptive separation and/or crystallization and reaction steps including transalkylation, isomerization, dealkylation etc. In typical aromatic complexes used to produce high purity $C_8$ aromatic isomers, the isomer-depleted raffinate stream from the separation process, either simulated moving bed adsorption or crystallization, is sent to an isomerization process in which the remaining xylene isomers are isomerized to produce the desired isomer (near equilibrium concentration) and convert ethylbenzene (EB) to other components which can be separated via fractionation or other means. Traditional BTX complexes use a vapor phase isomar catalyst. As such, the associated Isomar process requires a separator, compressor to recycle $H_2$, and distillation column to remove light gases.

Liquid Phase isomerization (LPI) processes have been proposed eliminates the need for the separator, compressor, column, and associated equipment. However, such liquid phase isomerization catalyst cannot handle ethylbenzene. Accordingly, such a LPI process requires the addition of auxiliary process to remove ethylbenzene, which cannot be handled by the LPI catalyst. Further, it will require integration of the LPI and the auxiliary process into an overall BTX process, which is quite complex and require sufficient optimization to maximize profitability.

Accordingly, it is desirable to provide improved methods and apparatuses for effective integration of the liquid phase isomerization process and the auxiliary process into the overall BTX process. Further, it is desirable to integrate the LPI and auxiliary process in BTX configuration so as to maximize profitability. Furthermore, other desirable features and characteristics of the present subject matter will become apparent from the subsequent detailed description of the subject matter and the appended claims, taken in conjunction with the accompanying drawing and this background of the subject matter.

BRIEF SUMMARY

Various embodiments contemplated herein relate to apparatuses and processes for integration of the LPI and reformate upgrading processes in an aromatics complex. The exemplary embodiments taught herein include apparatuses and processes for producing $C_8$ aromatic isomer product with integration of liquid phase isomerization and reformate upgrading process into the aromatics complex.

In accordance with another exemplary embodiment, a process is provided for producing a $C_8$ aromatic isomer product from a reformate stream, wherein the process comprises introducing a reformate stream comprising aromatic hydrocarbons to a reformate splitter column to provide a plurality of streams. A one or more streams comprising at least one stream from the plurality of streams is subjected to reformate upgrading conditions in a reformate upgrading unit to convert substantial portion of ethylbenzene to obtain an upgraded reformate stream. The upgraded reformate stream is passed to an aromatics stripper column to provide an aromatics stripper sidedraw stream comprising $C_8$ aromatic hydrocarbons and an aromatics stripper bottoms stream. The aromatics stripper sidedraw stream is passed to a xylene separation unit to provide the $C_8$ aromatic isomer product and a raffinate product stream comprising $C_8$ aromatic isomers. At least a first portion of the raffinate product stream is contacted with an isomerization catalyst in an isomerization unit in liquid phase at isomerization conditions in the substantial absence of hydrogen to obtain an isomerized stream.

In accordance with another exemplary embodiment, a process is provided for producing a $C_8$ aromatic isomer product from a reformate stream, wherein the process comprises introducing a reformate stream comprising aromatic hydrocarbons to a reformate splitter column to provide a reformate splitter bottoms stream comprising $C_{8+}$ aromatic hydrocarbons, a reformate splitter sidedraw stream comprising $C_8$ aromatic hydrocarbons and a reformate splitter overhead stream comprising $C_{7-}$ aromatic hydrocarbons. A one or more streams comprising the reformate splitter sidedraw stream is subjected to reformate upgrading conditions in a reformate upgrading unit to convert a substantial portion of ethylbenzene to obtain an upgraded reformate stream. The upgraded reformate stream is passed to an aromatics stripper column to provide an aromatics stripper sidedraw stream comprising $C_8$ aromatic hydrocarbons and an aromatics stripper bottoms stream. The aromatics stripper sidedraw stream is passed to a xylene separation unit to provide the $C_8$ aromatic isomer product and a raffinate product stream comprising $C_8$ aromatic isomers. At least a first portion of the raffinate product stream is contacted with an isomerization catalyst in an isomerization unit in liquid phase at isomerization conditions in the substantial absence of hydrogen to obtain an isomerized stream.

In accordance with yet another exemplary embodiment, an apparatus is provided for producing a $C_8$ aromatic isomer product from a reformate stream, wherein the apparatus comprises a reformate splitter column for fractionating a reformate stream comprising aromatic hydrocarbons to provide a plurality of streams. A reformate upgrading unit is in communication with the reformate splitter column for subjecting one or more streams comprising at least one stream from the plurality of streams to reformate upgrading conditions in a reformate upgrading unit to convert substantial portion of ethylbenzene to obtain an upgraded reformate stream in a upgraded reformate line. An aromatics stripper column is in communication with the reformate upgrading unit via the upgraded reformate line to provide an aromatics stripper sidedraw stream comprising $C_8$ aromatic isomers in a aromatics stripper sidedraw line and an aromatics stripper bottoms stream in an aromatics stripper bottoms line. A xylene separation unit is in communication with the aromatics stripper column via the aromatics stripper sidedraw line to provide the $C_8$ aromatic isomer product and a raffinate product stream comprising $C_8$ aromatic isomers in a raffinate product line. A liquid phase isomerization unit is in communication with a first raffinate product line for contacting at least a first portion of the raffinate product stream with an isomerization catalyst in an isomerization zone in liquid phase at isomerization conditions in the substantial absence of hydrogen to obtain an isomerized stream in an isomerized product line.

These and other features, aspects, and advantages of the present disclosure will become better understood upon consideration of the following detailed description, drawing and appended claims.

BRIEF DESCRIPTION OF THE DRAWING

The various embodiments will hereinafter be described in conjunction with the FIG. 1, wherein like numerals denote like elements.

FIG. 1 illustrates an aromatics complex having liquid phase isomerization and reformate upgrading process integrated into the aromatics complex in the process according to an embodiment of the present disclosure.

Corresponding reference characters indicate corresponding components throughout the several views of the drawing. Skilled artisans will appreciate that elements in FIG. 1 are illustrated for simplicity and clarity and have not necessarily been drawn to scale. For example, the dimensions of some of the elements in FIG. 1 may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

Definitions

As used herein, the term "stream" can include various hydrocarbon molecules and other substances.

As used herein, the term "stream", "feed", "product", "part" or "portion" can include various hydrocarbon molecules, such as straight-chain and branched alkanes, naphthenes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

As used herein, the term "overhead stream" can mean a stream withdrawn at or near a top of a vessel, such as a column.

As used herein, the term "bottoms stream" can mean a stream withdrawn at or near a bottom of a vessel, such as a column.

Hydrocarbon molecules may be abbreviated $C_1$, $C_2$, $C_3$, Cn where "n" represents the number of carbon atoms in the one or more hydrocarbon molecules or the abbreviation may be used as an adjective for, e.g., non-aromatics or compounds. Similarly, aromatic compounds may be abbreviated $A_6$, $A_7$, $A_8$, An where "n" represents the number of carbon atoms in the one or more aromatic molecules. Furthermore, a superscript "+" or "−" may be used with an abbreviated one or more hydrocarbons notation, e.g., $C_{3+}$ or $C_{3-}$, which is inclusive of the abbreviated one or more hydrocarbons. As an example, the abbreviation "$C_{3+}$" means one or more hydrocarbon molecules of three or more carbon atoms.

As used herein, the term "zone" or "unit" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top or overhead pressure is the pressure of the overhead vapor at the vapor outlet of the column. The bottom temperature is the liquid bottom outlet temperature. Overhead lines and bottoms lines refer to the net lines from the column downstream of any reflux or reboil to the column unless otherwise shown. Stripping columns omit a reboiler at a bottom of the column and instead provide heating requirements and separation impetus from a fluidized inert media such as steam.

As used herein, the term "rich" can mean an amount of at least generally 50%, and preferably 70%, by mole, of a compound or class of compounds in a stream.

As depicted, process flow lines in FIG. 1 can be referred to interchangeably as, e.g., lines, pipes, feeds, gases, products, discharges, parts, portions, or streams.

The term "communication" means that material flow is operatively permitted between enumerated components.

The term "downstream communication" means that at least a portion of material flowing to the subject in downstream communication may operatively flow from the object with which it communicates.

The term "direct communication" means that flow from the upstream component enters the downstream component without undergoing a compositional change due to physical fractionation or chemical conversion.

The term "substantial" can mean an amount of at least generally about 80%, preferably about 90%, and optimally about 99%, by weight, of a compound or class of compounds in a stream.

The term "passing" means that the material passes from a conduit or vessel to an object.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description. Moreover, the reaction conditions including selection of temperature, pressure, LHSV and catalyst in the various units in the aromatics complex described below are conventional which are known to one of ordinary skill in the art, unless wherever mentioned.

An exemplary embodiment of the process and apparatus for producing a $C_8$ aromatic isomer product in an aromatic complex is addressed with reference to a process and apparatus 100 illustrating an aromatics complex having liquid phase isomerization and reformate upgrading process integrated into the aromatics complex, according to an embodiment as shown in FIG. 1. The process and apparatus 100 includes a reformate splitter column 104, an aromatics stripper column 116, an aromatics rerun column 124, a xylene separation unit 130, an extract column 136, a xylene column 144, a raffinate column 150, an isomerization unit 162, an aromatics extraction unit 170, a clay treater 176, a benzene-toluene (BT) column 180, a transalkylation unit 190, a transalkylation stripper 194, a stabilizer 202 and a heavy aromatics column 208.

In accordance with an exemplary embodiment as shown in FIG. 1, a reformate stream in line 102 comprising aromatic hydrocarbons may be introduced to the reformate splitter column 104 to provide a plurality of streams via fractionation. In accordance with an exemplary embodiment as shown in FIG. 1, a reformate splitter overhead stream comprising $C_{7-}$ aromatic hydrocarbons in reformate overhead line 106, a reformate splitter sidedraw stream comprising $C_8$ aromatic hydrocarbons in reformate sidedraw line 108 and a reformate splitter bottoms stream comprising $C_{8+}$ aromatic hydrocarbons in reformate bottoms line 110 are withdrawn from the reformate splitter column 104. In accordance with an instant embodiment as shown, an overhead stream from the reformate splitter column 104 may be condensed and separated in a receiver with a portion of the condensed liquid being refluxed back to the reformate splitter column 104 to obtain the reformate splitter overhead stream from a net portion in line 106. Further, as illustrated, the reformate splitter column 104 may include a reboiler at a bottom of the column to vaporize and send a portion of the reformate splitter bottoms stream back to the bottom of the column.

Subsequently, at least one stream from the plurality of streams may be passed to the reformate upgrading unit 112. In accordance with an exemplary embodiment as shown in FIG. 1, the reformate splitter sidedraw stream in reformate sidedraw line 108 may be passed to the reformate upgrading unit 112. Accordingly, the reformate upgrading unit 112 may be in direct, downstream communication with the reformate splitter column 104. Further, an aromatics rerun column overhead stream in line 126 obtained from the aromatics rerun column 124 and a second portion of the raffinate product stream in second raffinate product line 158 obtained from the raffinate column 150 may also be passed to the reformate upgrading unit 112. Accordingly, in the instant aspect, the one or more streams may comprise the reformate splitter sidedraw stream, the aromatics rerun column overhead stream and the portion of the raffinate product stream. The one or more streams may be subjected to reformate upgrading conditions in the reformate upgrading unit 112 to convert substantial portion of ethylbenzene present in the one or more streams to obtain an upgraded reformate stream in upgraded reformate line 114. The reformate upgrading 112 unit can remove a substantial portion of ethylbenzene via conversion to other hydrocarbons such as benzene. As shown in FIG. 1, both the reformate splitter sidedraw stream and the aromatics rerun overhead stream may be passed to the reformate upgrading unit 112. In such an aspect, a substantial amount of $C_8$ olefins will be removed from the upgraded reformate stream. Accordingly, the instant process as shown in FIG. 1 does not require a clay treater downstream of the reformate upgrading unit 112.

The upgraded reformate stream in the upgraded reformate line 114 may be passed to the aromatics stripper column 116 for separation. Accordingly, the aromatics stripper column 116 may be in downstream communication with the reformate upgrading unit 112 via the upgraded reformate line 114. At least a portion of an isomerized stream may also be passed to the aromatics stripper column 116. In accordance with an exemplary embodiment as shown in FIG. 1, a second portion of the isomerized stream in second isomerized product line 168 may be passed to the aromatics stripper column 116. Further, in accordance with an exemplary embodiment as shown in FIG. 1, a BT column bottoms stream in line 188 and a xylene column bottoms stream in line 148 may be passed to the aromatics stripper column 116. The incoming feedstreams undergo separation in the aromatics stripper column 116 and an aromatics stripper overhead stream in line 118 comprising $C_7$ and lighter hydrocarbons, an aromatics stripper sidedraw stream comprising $C_8$ aromatic hydrocarbons in line 120 and an aromatics stripper bottoms stream comprising $C_{8+}$ aromatic hydrocarbons in line 122 are withdrawn from the aromatics stripper column 116. In accordance with an exemplary embodiment, the aromatics stripper column 116 may be a divided wall column. Applicants have found that the divided wall column results in more efficient removal of $C_{9+}$ aromatic hydrocarbons from the aromatics stripper sidedraw stream being passed to the xylene separation unit 130. As the presence of $C_{9+}$ aromatic hydrocarbons contaminates the $C_8$ aromatic isomer product to be obtained from the xylene separation unit 130, use of a divided wall column improves the efficiency of the xylene separation unit and results in better product quality. In various embodiments, the amount of $C_9$ and higher aromatic hydrocarbons present in the feed to the para-xylene unit 130 is less than 1 wt %.

Referring back to the reformate splitter column 104, the reformate splitter bottoms stream in line 110 may be passed to the aromatics rerun column 124. Further, the aromatics stripper bottoms stream in line 122 may also be passed to the aromatics rerun column 124. The aromatics rerun column overhead stream in line 126, an aromatics rerun column sidedraw stream in line 127 and an aromatic rerun column bottoms stream in line 128 are withdrawn from the aromatics rerun column 124. The aromatics rerun column overhead stream in line 126 is rich in $C_8$ aromatic hydrocarbons and may be passed to the reformate upgrading unit 112 to recover additional C8 aromatic hydrocarbons.

Referring back to aromatics stripper column 116, the aromatics stripper sidedraw stream comprising $C_8$ aromatic hydrocarbons in line 120 may be passed to the xylene separation unit 130 to provide the $C_8$ aromatic isomer product and a raffinate product stream comprising $C_8$ aromatic isomers. The aromatics stripper sidedraw stream in line 120 including para-xylene, meta-xylene and ortho-xylene may be passed to the xylene separation unit 130 to obtain a desired C$_8$ aromatic isomer product via a separation process. The xylene separation unit 130 may be one of a para-xylene separation unit, a meta-xylene separation unit or an ortho-xylene separation unit depending on the C$_8$ aromatic product desired and the operating conditions can be tailored accordingly. In accordance with an exemplary embodiment as discussed, the xylene separation unit 130 is a para-xylene separation unit and will be referred to as the para-xylene separation unit 130 for the purpose of the discussion of the instant embodiment. In accordance with an exemplary embodiment as shown in FIG. 1, a first portion of the isomerized stream in first isomerized product line 166 may also be passed to the para-xylene separation unit 130. In accordance with the instant embodiment as discussed, the separation process in the para-xylene separation unit 130 operates, preferably via simulated moving adsorption bed (SMB) employing a desorbent, to provide a xylene extract stream in line 132 which is para-xylene extract stream comprising a mixture of para-xylene and desorbent for the instant embodiment. In accordance with various embodiments, the desorbent may be any aromatic hydrocarbon with a lower boiling point than the C$_8$ aromatic isomers. In accordance with the instant embodiment, toluene is used as the desorbent.

The para-xylene extract stream in line 132 may be passed to the extract column 136 which separates para-xylene from the desorbent. A para-xylene stream in line 140 may be withdrawn comprising the desired para-xylenes from the extract column 136. Further, a first return desorbent stream in line 142 is withdrawn which may be subsequently recycled to the para-xylene separation unit 130. In an aspect as shown in FIG. 1, a desorbent drag stream in line 138 may also be withdrawn from the extract column 136. In accordance with an exemplary embodiment, the desorbent drag stream in line 138 may comprise primarily C$_{7-}$ hydrocarbons and may be passed to the BT column 180. The para-xylene stream in line 140 may be passed to the xylene column 144. In accordance with the instant embodiment as discussed, the xylene column is a para-xylene column. The para-xylene column 144 may separate the para-xylene product in line 146 from the heavier hydrocarbons obtained as a bottoms stream in line 148 which may be subsequently recycled to the aromatics stripper column 116 and processed further as previously described to maximize para-xylene recovery. In accordance with an instant embodiment as shown, an overhead stream from the para-xylene column 144 may be condensed and separated with a portion of the condensed liquid being refluxed back to the para-xylene column 146 to obtain the para-xylene product from a net portion in line 146. Further, as illustrated, the para-xylene column 144 may include a reboiler at a bottom of the column to vaporize and send a portion of the bottoms stream back to the bottom of the column. In an aspect, pressure in para-xylene column 144 is approximately about 60 psig. In such an aspect, the condenser of the para-xylene column 144 can be used to reboil the reformate splitter column 104 with the use of high flux tubes. In another aspect, such high flux tubes may be used on the para-xylene column 144 so that high pressure steam can be used as a heat source. Accordingly, the present disclosure reduces overall steam use.

A raffinate stream in line 134 comprising non-equilibrium mixture of C$_8$ aromatics raffinate and the desorbent may be also withdrawn from the para-xylene separation unit 130. The raffinate stream in line 134 may be passed to the raffinate column 150. In accordance with an exemplary embodiment as shown in FIG. 1, a second toluene-enriched stream in line 186 from the BT column 180 may also be introduced to the raffinate column 150 which may act as a makeup for the toluene being used as the desorbent in the para-xylene separation process as per the instant embodiment. The raffinate column 150 separates a raffinate product stream in line 156 for isomerization in isomerization unit 162 from a second return desorbent stream in line 152. In accordance with an exemplary embodiment as shown in FIG. 1, the first desorbent return stream in line 142 and the second desorbent return stream in line 152 may combine to provide a combined desorbent return stream in line 154 which may be subsequently passed to the para-xylene separation unit 130.

At least a portion of the raffinate product stream in line 156 comprising a non-equilibrium mixture of xylene isomers is introduced to the isomerization unit 162 to provide an isomerized stream in line 164. In accordance with an exemplary embodiment as shown in FIG. 1, a first portion of the raffinate product stream in first raffinate product line 160 is contacted with an isomerization catalyst in the isomerization unit 162 in liquid phase at isomerization conditions in the substantial absence of hydrogen to obtain the isomerized stream in line 164. Accordingly, in various embodiments, the isomerization unit 162 may be referred to as the liquid phase isomerization (LPI) unit.

The isomerization unit 162 comprises isomerization targeted specifically to the isomerization of xylenes in the feedstock to a near-equilibrium mixture with minimal conversion to lighter and heavier products. The isomerization conditions may comprise temperature ranging from about 100° C. to about 500° C., and preferably from about 200° C. to 400° C. The pressure is from about 500 kPa to about 5 MPa absolute. The isomerization unit contains a sufficient volume of catalyst to provide a liquid hourly space velocity with respect to the feed stream of from about 0.5 hr$^{-1}$ to 50 hr$^{-1}$, and preferably 0.5 hr$^{-1}$ to 20 hr$^{-1}$. The isomerization is carried out in the presence of minimal hydrogen, i.e., the amount of hydrogen present is less than about 0.2 moles/mole of feed. In accordance with an exemplary embodiment, the isomerization is carried out in the substantial absence of hydrogen and in the liquid phase with no free hydrogen being added to the feed stream; in this event, any dissolved hydrogen from prior processing is substantially less than 0.05 moles/mole of feed, frequently less than 0.01 moles/mole, and possibly not detectable by usual analytical means.

The isomerization unit 162 may comprise a single reactor or two or more separate reactors with suitable means there between to ensure that the desired isomerization temperature is maintained at the entrance to each reactor. The reactants may be contacted with the catalyst bed in upward-, downward-, or radial-flow fashion.

The isomerization catalyst favorably comprises a zeolitic aluminosilicate selected from those which have a Si:Al$_2$ ratio greater than about 10, preferably greater than 20, and a pore diameter of about 5 to 8 angstroms (Å). Specific examples of suitable zeolites are the MFI, MEL, EUO, FER, MFS, MTT, MTW, TON, MOR and FAU types of zeolites. A particularly favored MFI-type zeolite is gallium-MFI, with gallium as a component of the crystal structure. A preferred Ga-MFI has a Si/Ga2 mole ratio of less than 500, and preferably less than 100; the aluminum content concomitantly is very low, with an Si/Al2 mole ratio of greater than 500 and preferably greater than 1000. The proportion of zeolite in the catalyst generally is in the range of from about 1 wt % to 99 wt %, and preferably from about 25 wt % to about 75 wt %. The isomerization catalyst may contain from about 0.01 wt % to 2.0 wt % of a platinum-group metal, favorably platinum, but preferably has the substantial absence of a metallic compound. An inorganic-oxide binder, preferably alumina, comprises the balance of the catalyst. A preferred catalyst shape is a sphere, with an alternative suitable shape being an extrudate.

In accordance with an exemplary embodiment as shown in FIG. 1, the second portion of the raffinate product stream in second raffinate product line 158 is passed to the reformate upgrading unit 112 and processed further as previously described. In accordance with various embodiments, the first portion of the raffinate product stream may vary from 0 to 100% with remainder being the second portion of the raffinate product stream.

Referring back to the isomerization unit 162, in the instant process as discussed for the production of para-xylene, the LPI process converts m-xylene and o-xylene in the raffinate product stream for partial conversion back to p-xylene. It is an advantage that LPI uniquely operates without $H_2$ addition so that no light gases are present in the isomerization product. Accordingly, a portion of the isomerized stream can be passed to directly to the para-xylene unit 130 and another portion can be sent to aromatics stripper column 116 to remove heavier components along with some benzene and toluene. As shown in FIG. 1, the isomerized stream in line 164 may be withdrawn from the isomerization unit 162. The first portion of isomerized stream in first isomerized product line 166 may be passed directly to the para-xylene separation unit 130 and processed further as previously described. Accordingly, the para-xylene separation unit 130 may be in direct, downstream communication with the isomerization unit 162 via the first isomerized product line 166. The second portion of the isomerized stream in second isomerized product line 168 may be passed to the aromatics stripper column 116 and processed further as previously described. Accordingly, as a portion of the isomerized stream is passed directly to the para-xylene unit 130 in the present disclosure, amount of feed to the aromatics stripper column 116 is reduced. The instant arrangement provides an advantage as lowering the feed to the aromatics stripper column 116 reduces reboiler heat need and column size.

Referring back to the reformate splitter column 104, the reformate splitter overhead stream in reformate overhead line 106 comprising $C_{7-}$ aromatic hydrocarbons may be passed to an aromatics-extraction and a fractionation step to provide a benzene product stream and a toluene enriched stream. The reformate overhead stream in reformate overhead line 106 may be passed to the aromatics extraction unit 170. The aromatics extraction unit 170 can comprise different methods of separating aromatics from a hydrocarbon stream. One industry standard is the Sulfolane™ process, which is an extractive distillation process utilizing sulfolane to facilitate high purity extraction of aromatics. The Sulfolane™ process is well known to those skilled in the art. An aromatics extract stream in line 174 comprising benzene and toluene and a raffinate stream in line 172 comprising non-aromatic hydrocarbons may be withdrawn from the aromatics extraction unit 170. The aromatics extract stream in line 174 may be passed to the BT column 180 to provide benzene and toluene via separation. In accordance with an exemplary embodiment as shown in FIG. 1, the aromatics extract stream in line 174 may be passed through a clay treater 176 to treat residual olefin contaminants and provide a treated aromatics extract stream in line 178 prior to being passed to the BT column 180. A transalkylation stripper bottoms stream in line 198 from the transalkylation stripper column 194 may also be passed to the BT column 180. A benzene-enriched stream in line 182, a first toluene-enriched stream in line 184 and the second toluene-enriched stream in line 186 are withdrawn from the BT column 180. Further, the BT column bottoms stream in line 188 is withdrawn and sent to the aromatics stripper column 116 for further processing as previously described. The second toluene-enriched stream in line 186 may be passed to the raffinate column 150. The first toluene-enriched stream in line 184 may be passed to the transalkylation unit 190 for production of additional xylenes and benzene.

In accordance with an exemplary embodiment as shown in FIG. 1, in addition to first toluene-enriched stream, the aromatics rerun column sidedraw stream in line 127 rich in $C_9$ and $C_{10}$ alkylaromatics may be passed to the transalkylation unit 190 along with a heavy aromatics column overhead stream in line 210 rich in $C_9$ and $C_{10}$ alkylaromatics from the heavy aromatics column 208. A make-up hydrogen gas stream (not shown) may also be provided to the transalkylation unit 190. In the transalkylation unit 190, the incoming feedstreams may be contacted with a transalkylation catalyst under transalkylation conditions. In the transalkylation unit 190, the process continues by transalkylating $C_9$ and $C_{10}$ alkylaromatics with toluene. A transalkylated stream in line 192 comprising benzene and xylenes may be withdrawn from the transalkylation unit 190. In accordance with an exemplary embodiment, the reformate upgrading unit 112 and the transalkylation unit 190 share a common compressor.

Transalkylation catalysts that can be used in the present disclosure include conventional transalkylation catalysts such as those disclosed in U.S. Pat. No. 6,740,788, the teachings of which are incorporated herein by reference. Conditions employed in the transalkylation unit 190 normally include a temperature of from about 200° C. to about 540° C. The transalkylation unit 190 is operated at moderately elevated pressures broadly ranging from about 1 kg/cm² to about 60 kg/cm². The transalkylation reaction can be effected over a wide range of space velocities, with higher space velocities affecting a higher ratio of para-xylene at the expense of conversion. Liquid hourly space velocity generally is in the range of from about 0.1 hr$^{-1}$ to about 20 hr$^{-1}$.

The transalkylated stream in line 192 may be sent to transalkylation stripper 194 to recover the transalkylation stripper bottoms stream in line 198. Light ends may be removed in transalkylation stripper overhead stream in line 196 and a net overhead stream in line 200 comprising $C_6$ and lighter hydrocarbons may also be withdrawn from the transalkylation stripper 194. Subsequently, the transalkylation stripper bottoms stream in line 198 may be recycled to the BT column 180 to recover benzene product and unconverted toluene for further processing as previously described. The net overhead stream in line 200 along with the aromatics stripper overhead stream in line 118 may be passed to the stabilizer 202 to provide a stabilizer overhead vaporous stream in line 204 and a stabilizer bottoms stream in line 206. In various embodiments, the stabilizer bottoms stream in line 206 may be passed to the aromatics extraction unit 170. In other embodiments, the stabilizer bottoms stream 206 may be passed to the transalkylation stripper 194.

Referring back to the aromatics rerun column 124, the aromatic rerun column bottoms stream in line 128 rich in $C_9$ and heavier alkylaromatic hydrocarbons is passed to the heavy aromatics column 208 to separate heavy aromatics comprising $C_{11+}$ alkylaromatic hydrocarbons from $C_9$ and $C_{10}$ alkylaromatics recovered as the heavy aromatics column overhead stream in line 210. The $C_{11+}$ alkylaromatic hydrocarbons may be withdrawn from the heavy aromatics column 208 as a bottoms stream in line 212. The heavy aromatics column overhead stream in line 210 rich in $C_9$ and $C_{10}$ alkylaromatics may be passed to the transalkylation unit 190 for production of additional xylenes and benzene as previously described.

SPECIFIC EMBODIMENTS

While the following is described in conjunction with specific embodiments, it will be understood that this description is intended to illustrate and not limit the scope of the preceding description and the appended claims.

A first embodiment of the invention is a process for producing a $C_8$ aromatic isomer product from a reformate stream, wherein the process comprises introducing a reformate stream comprising aromatic hydrocarbons to a reformate splitter column to provide a plurality of streams; subjecting one or more streams comprising at least one stream from the plurality of streams to reformate upgrading conditions in a reformate upgrading unit to convert substantial portion of ethylbenzene to obtain an upgraded reformate stream; passing the upgraded reformate stream to an aromatics stripper column to provide an aromatics stripper sidedraw stream comprising $C_8$ aromatic hydrocarbons and an aromatics stripper bottoms stream; passing the aromatics stripper sidedraw stream to a xylene separation unit to provide the $C_8$ aromatic isomer product and a raffinate product stream comprising $C_8$ aromatic isomers; and contacting at least a first portion of the raffinate product stream with an isomerization catalyst in an isomerization unit in liquid phase at isomerization conditions in the substantial absence of hydrogen to obtain an isomerized stream. An embodiment of the invention is one, any or all of prior embodiments in this paragraph up through the first embodiment in this paragraph further comprising passing at least a first portion of the isomerized stream to the xylene separation unit and passing at least a second portion of the isomerized stream to the aromatics stripper column. An embodiment of the invention is one, any or all of prior embodiments in this paragraph up through the first embodiment in this paragraph, wherein the plurality of streams comprise a reformate splitter bottoms stream comprising $C_{8+}$ aromatic hydrocarbons, a reformate splitter sidedraw stream comprising $C_8$ aromatic hydrocarbons and a reformate splitter overhead stream comprising $C_{7-}$ aromatic hydrocarbons and the at least one stream being the reformate splitter sidedraw stream. An embodiment of the invention is one, any or all of prior embodiments in this paragraph up through the first embodiment in this paragraph further comprising passing the reformate splitter bottoms stream and the aromatics stripper bottoms stream to an aromatics rerun column to provide a aromatics rerun column overhead stream comprising $C_8$ aromatic hydrocarbons. An embodiment of the invention is one, any or all of prior embodiments in this paragraph up through the first embodiment in this paragraph further comprising passing the aromatics rerun column overhead stream and a second portion of the raffinate product stream to the reformate upgrading unit. An embodiment of the invention is one, any or all of prior embodiments in this paragraph up through the first embodiment in this paragraph further comprising passing the reformate splitter overhead stream to an aromatics-extraction and a fractionation step to provide a benzene product stream and a toluene enriched stream. An embodiment of the invention is one, any or all of prior embodiments in this paragraph up through the first embodiment in this paragraph further comprising passing the toluene enriched stream and an aromatics rerun column sidedraw stream rich in $C_9$ and $C_{10}$ alkylaromatics from the aromatics rerun column to a transalkylation unit. An embodiment of the invention is one, any or all of prior embodiments in this paragraph up through the first embodiment in this paragraph, wherein the reformate upgrading unit and transalkylation unit share a common compressor. An embodiment of the invention is one, any or all of prior embodiments in this paragraph up through the first embodiment in this paragraph wherein the aromatics stripper column is divided wall column. An embodiment of the invention is one, any or all of prior embodiments in this paragraph up through the first embodiment in this paragraph, wherein the xylene separation unit is a simulated moving bed adsorption unit. An embodiment of the invention is one, any or all of prior embodiments in this paragraph up through the first embodiment in this paragraph, wherein the xylene separation unit uses a desorbent with a lower boiling point than the $C_8$ aromatic isomers. An embodiment of the invention is one, any or all of prior embodiments in this paragraph up through the first embodiment in this paragraph, wherein the desorbent is toluene. An embodiment of the invention is one, any or all of prior embodiments in this paragraph up through the first embodiment in this paragraph, wherein the $C_8$ aromatic isomer product is one of a para-xylene or meta-xylene.

A second embodiment of the invention is a process for producing a $C_8$ aromatic isomer product from a reformate stream, wherein the process comprises introducing a reformate stream comprising aromatic hydrocarbons to a reformate splitter column to provide a reformate splitter bottoms stream comprising $C_{8+}$ aromatic hydrocarbons, a reformate splitter sidedraw stream comprising $C_8$ aromatic hydrocarbons and a reformate splitter overhead stream comprising $C_{7-}$ aromatic hydrocarbons; subjecting one or more streams comprising the reformate splitter sidedraw stream to reformate upgrading conditions in a reformate upgrading unit to convert substantial portion of ethylbenzene to obtain an upgraded reformate stream; passing the upgraded reformate stream to an aromatics stripper column to provide an aromatics stripper sidedraw stream comprising $C_8$ aromatic hydrocarbons and an aromatics stripper bottoms stream; passing the aromatics stripper sidedraw stream to a xylene separation unit to provide the $C_8$ aromatic isomer product and a raffinate product stream comprising $C_8$ aromatic isomers; and contacting at least a first portion of the raffinate product stream with an isomerization catalyst in an isomerization unit in liquid phase at isomerization conditions in the substantial absence of hydrogen to obtain an isomerized stream. An embodiment of the invention is one, any or all of prior embodiments in this paragraph up through the second embodiment in this paragraph further comprising passing at least a portion of the isomerized stream to the xylene separation unit. An embodiment of the invention is one, any or all of prior embodiments in this paragraph up through the second embodiment in this paragraph further comprising passing the reformate splitter bottoms stream and the aromatics stripper bottoms stream to an aromatics rerun column to provide a aromatics rerun column overhead stream comprising $C_8$ aromatic hydrocarbons. An embodiment of the invention is one, any or all of prior embodiments in this paragraph up through the second embodiment in this paragraph further comprising passing the aromatics rerun column overhead stream and a second portion of the raffinate product stream to the reformate upgrading unit. An embodiment of the invention is one, any or all of prior embodiments in this paragraph up through the second embodiment in this paragraph further comprising passing the reformate splitter overhead stream to an aromatics-extraction and a fractionation step to provide a benzene product stream and a toluene enriched stream. An embodiment of the invention is one, any or all of prior embodiments in this paragraph up through the second embodiment in this paragraph further comprising passing the toluene enriched stream and an aromatics rerun column sidedraw stream rich in $C_9$ and $C_{10}$ alkylaromatics from the aromatics rerun column to a transalkylation unit. An embodiment of the invention is one, any or all of prior embodiments in this paragraph up through the second embodiment in this paragraph, wherein the reformate upgrading unit and transalkylation unit share a common compressor.

A third embodiment of the invention is an apparatus for producing a $C_8$ aromatic isomer product from a reformate stream, wherein the apparatus comprises a reformate splitter column for fractionating a reformate stream comprising aromatic hydrocarbons to provide a plurality of streams; a reformate upgrading unit in communication with the reformate splitter column for subjecting one or more streams comprising at least one stream from the plurality of streams to reformate upgrading conditions in a reformate upgrading unit to convert substantial portion of ethylbenzene to obtain an upgraded reformate stream in a upgraded reformate line; an aromatics stripper column in communication with the reformate upgrading unit via the upgraded reformate line to provide an aromatics stripper sidedraw stream comprising $C_8$ aromatic isomers in a aromatics stripper sidedraw line and an aromatics stripper bottoms stream in an aromatics stripper bottoms line; a xylene separation unit in communication with the aromatics stripper column via the aromatics stripper sidedraw line to provide the $C_8$ aromatic isomer product and a raffinate product stream comprising $C_8$ aromatic isomers in a raffinate product line; and a liquid phase isomerization unit in communication with a first raffinate product line for contacting at least a first portion of the raffinate product stream with an isomerization catalyst in an isomerization zone in liquid phase at isomerization conditions in the substantial absence of hydrogen to obtain an isomerized stream in an isomerized product line. An embodiment of the invention is one, any or all of prior embodiments in this paragraph up through the third embodiment in this paragraph, wherein the plurality of streams comprise a reformate splitter bottoms stream comprising $C_{8+}$ aromatic hydrocarbons in a reformate bottoms line, a reformate splitter sidedraw stream comprising $C_8$ aromatic hydrocarbons in a reformate sidedraw line and a reformate splitter overhead stream comprising $C_{7-}$ aromatic hydrocarbons in a reformate overhead line, the reformate upgrading unit being in downstream communication with the reformate sidedraw line. An embodiment of the invention is one, any or all of prior embodiments in this paragraph up through the third embodiment in this paragraph, further comprising a an aromatics extraction unit in communication with reformate overhead line; and a benzene-toluene (BT) column in communication with aromatics extraction unit. An embodiment of the invention is one, any or all of prior embodiments in this paragraph up through the third embodiment in this paragraph further comprising a transalkylation unit in communication with the BT column and an aromatics rerun column. An embodiment of the invention is one, any or all of prior embodiments in this paragraph up through the third embodiment in this paragraph, wherein the reformate upgrading unit and transalkylation unit share a common compressor. An embodiment of the invention is one, any or all of prior embodiments in this paragraph up through the third embodiment in this paragraph, wherein the xylene separation unit is in direct communication with the isomerization unit via a first isomerized product line comprising at least a portion of the isomerized stream.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for producing a $C_8$ aromatic isomer product from a reformate stream, wherein the process comprises:
    (a) introducing a reformate stream comprising aromatic hydrocarbons to a reformate splitter column to provide a reformate splitter bottoms stream comprising $C_{8+}$ aromatic hydrocarbons, a reformate splitter sidedraw stream comprising $C_8$ aromatic hydrocarbons, and a reformate splitter overhead stream comprising $C_{7-}$ aromatic hydrocarbons;
    (b) subjecting at least the reformate splitter sidedraw stream to reformate upgrading conditions in a reformate upgrading unit to convert a portion of ethylbenzene to obtain an upgraded reformate stream, wherein the reformate upgrading unit and a transalkylation unit share a common compressor;
    (c) passing the upgraded reformate stream to an aromatics stripper column to provide an aromatics stripper sidedraw stream comprising $C_8$ aromatic hydrocarbons and an aromatics stripper bottoms stream;
    (d) passing the aromatics stripper sidedraw stream to a xylene separation unit to provide the $C_8$ aromatic isomer product and a raffinate product stream comprising $C_8$ aromatic isomers;
    (e) contacting at least a first portion of the raffinate product stream with an isomerization catalyst in an isomerization unit in liquid phase at isomerization conditions in the absence of hydrogen to obtain an isomerized stream;
    (f) passing at least a first portion of the isomerized stream to the xylene separation unit;
    (g) passing at least a second portion of the isomerized stream to the aromatics stripper column;
    (h) passing the aromatics stripper bottoms stream and the reformate splitter bottoms stream to an aromatics rerun column to provide an aromatics rerun column overhead stream comprising $C_8$ aromatic hydrocarbons including ethylbenzene; and
    (i) passing the aromatics rerun column overhead stream and a second portion of the raffinate product stream to the reformate upgrading unit.

2. The process of claim 1 further comprising:
    passing the reformate splitter overhead stream to an aromatics-extraction step to produce an aromatics extract stream comprising benzene and toluene, and
    passing the aromatics extract stream to a fractionation step to provide a benzene product stream and a toluene enriched stream.

3. The process of claim 2 further comprising passing the toluene enriched stream and an aromatics rerun column sidedraw stream rich in $C_9$ and $C_{10}$ alkylaromatics from the aromatics rerun column to the transalkylation unit.

4. The process of claim 1 wherein the aromatics stripper column is divided wall column.

5. The process of claim 1 wherein the xylene separation unit is a simulated moving bed adsorption unit.

6. The process of claim 5 wherein the xylene separation unit uses a desorbent with a lower boiling point than the $C_8$ aromatic isomers.

7. The process of claim 6 wherein the desorbent is toluene.

8. The process of claim 1 wherein the $C_8$ aromatic isomer product is one of para-xylene or meta-xylene.

9. A process for producing a $C_8$ aromatic isomer product from a reformate stream, wherein the process comprises:
   (a) introducing a reformate stream comprising aromatic hydrocarbons to a reformate splitter column to provide a reformate splitter bottoms stream comprising $C_{8+}$ aromatic hydrocarbons, a reformate splitter sidedraw stream comprising $C_8$ aromatic hydrocarbons and a reformate splitter overhead stream comprising $C_{7-}$ aromatic hydrocarbons;
   (b) subjecting the reformate splitter sidedraw stream to reformate upgrading conditions in a reformate upgrading unit to convert a portion of ethylbenzene to obtain an upgraded reformate stream, wherein the reformate upgrading unit and a transalkylation unit share a common compressor;
   (c) passing the upgraded reformate stream to an aromatics stripper column to provide an aromatics stripper sidedraw stream comprising $C_8$ aromatic hydrocarbons and an aromatics stripper bottoms stream, wherein the aromatic stripper column comprises a divided wall column;
   (d) passing the aromatics stripper sidedraw stream to a xylene separation unit to provide the $C_8$ aromatic isomer product and a raffinate product stream comprising $C_8$ aromatic isomers;
   (e) contacting at least a first portion of the raffinate product stream with an isomerization catalyst in an isomerization unit in liquid phase at isomerization conditions in the absence of hydrogen to obtain an isomerized stream;
   (f) passing the aromatics stripper bottoms stream and the reformate splitter bottoms stream comprising $C_{8+}$ aromatic hydrocarbons to an aromatics rerun column;
   (g) passing a bottoms stream from the aromatics rerun column to a heavy aromatics column;
   (h) passing a first portion of the isomerized stream to the xylene separation unit; and
   (i) passing a second portion of the raffinate product stream and an aromatics rerun column overhead stream comprising $C_8$ aromatic hydrocarbons to the reformate upgrading unit.

10. The process of claim 9 further comprising:
   passing the reformate splitter overhead stream to an aromatics-extraction step to produce an aromatics extract stream comprising benzene and toluene, and
   passing the aromatics extract stream to a fractionation step to provide a benzene product stream and a toluene enriched stream.

11. The process of claim 10 further comprising passing the toluene enriched stream and an aromatics rerun column sidedraw stream rich in $C_9$ and $C_{10}$ alkylaromatics from the aromatics rerun column to the transalkylation unit.

* * * * *